United States Patent
Schmidt et al.

(10) Patent No.: US 11,701,021 B2
(45) Date of Patent: Jul. 18, 2023

(54) LESION ASSESSMENT USING PEAK-TO-PEAK IMPEDANCE AMPLITUDE MEASUREMENT

(71) Applicant: Medtronic, Inc., Minneapolis, MN (US)

(72) Inventors: Megan Schmidt, Blaine, MN (US); Lars Mattison, St. Anthony, MN (US)

(73) Assignee: Medtronic, Inc., Minneapolis, MN (US)

( * ) Notice: Subject to any disclaimer, the term of this patent is extended or adjusted under 35 U.S.C. 154(b) by 946 days.

(21) Appl. No.: 16/598,400

(22) Filed: Oct. 10, 2019

(65) Prior Publication Data

US 2021/0106249 A1    Apr. 15, 2021

(51) Int. Cl.
*A61B 5/053*    (2021.01)
*A61B 5/00*    (2006.01)
(Continued)

(52) U.S. Cl.
CPC ............ *A61B 5/053* (2013.01); *A61B 5/6853* (2013.01); *A61B 18/1492* (2013.01);
(Continued)

(58) Field of Classification Search
CPC .......................................... A61B 2018/00845
See application file for complete search history.

(56) References Cited

U.S. PATENT DOCUMENTS 6,663,627 B2    12/2003  Francischelli et al.
8,403,925 B2     3/2013  Miller et al.
(Continued)

FOREIGN PATENT DOCUMENTS

WO    2016081650 A1    5/2016

OTHER PUBLICATIONS

International Search Report and Written Opinion dated Dec. 2, 2020, for corresponding International Application No. PCT/US2020/051802; International Filing Date: Sep. 21, 2020 consisting of 14-pages.

*Primary Examiner* — Ronald Hupczey, Jr.
(74) *Attorney, Agent, or Firm* — Michael Best & Friedrich LLP (57) ABSTRACT

A method and system for lesion formation assessment in tissue that has undergone an ablation procedure. In one embodiment, a method of assessing lesion formation comprises: recording a baseline impedance measurement from an area of tissue with a medical device; ablating the area of tissue with the medical device; recording a post-treatment impedance measurement from the area of tissue with the medical device; identifying at least one amplitude characteristic of the baseline impedance measurement and identifying at least one amplitude characteristic of the post-treatment impedance measurement; comparing the at least one amplitude characteristic of the baseline impedance measurement and the at least one amplitude characteristic of the post-treatment impedance measurement; generating an indication of efficacy based on the comparison, the indication of efficacy being one of sufficient lesion formation and insufficient lesion formation; and re-ablating the area of tissue if the indication of efficacy is insufficient lesion formation.

20 Claims, 4 Drawing Sheets

(51) Int. Cl.
*A61B 18/14* (2006.01)
*A61B 90/00* (2016.01)
*A61B 18/00* (2006.01)

(52) U.S. Cl.
CPC ............... *A61B 2018/00577* (2013.01); *A61B 2018/00791* (2013.01); *A61B 2018/00875* (2013.01); *A61B 2090/065* (2016.02)

(56) References Cited

U.S. PATENT DOCUMENTS

| | | |
|---|---|---|
| 9,339,325 B2 | 5/2016 | Miller et al. |
| 9,743,854 B2 | 8/2017 | Stewart et al. |
| 2003/0130711 A1* | 7/2003 | Pearson ............. A61B 18/1477 607/101 |
| 2007/0062547 A1* | 3/2007 | Pappone ............ A61B 18/1233 606/41 |
| 2012/0029504 A1* | 2/2012 | Afonso ............... A61B 18/1492 606/34 |
| 2012/0197243 A1 | 8/2012 | Sherman et al. |
| 2014/0275993 A1 | 9/2014 | Ballakur |
| 2016/0199126 A1 | 7/2016 | Satake |
| 2018/0310978 A1* | 11/2018 | Avitall .................. A61B 5/287 |

* cited by examiner

LESION ASSESSMENT USING PEAK-TO-PEAK IMPEDANCE AMPLITUDE MEASUREMENT

CROSS-REFERENCE TO RELATED APPLICATION n/a

FIELD

The present technology is generally related to lesion formation assessment in tissue that has undergone one or more ablation procedures. In particular, the present technology is related to using impedance measurements, in the form of peak-to-peak amplitude within the cardiac cycle, to evaluate lesion formation.

BACKGROUND

Radiofrequency (RF) and cryogenic ablation procedures are well recognized treatments for vascular and cardiac diseases such as arrhythmia, including atrial fibrillation. The application of either RF or cryogenic treatment is usually based on the preference of the surgeon or the specific tissue to be treated. In either RF or cryogenic ablation, however, the location and quality of the lesion produced is a primary concern. The clinical success of cardiac tissue ablation to treat arrhythmias depends on efficacy and safety of the application of the selected energy. Many factors influence lesion size such as tissue-electrode contact force, ablation energy level, and cooling factors, that is, blood flow rate, tissue perfusion, and the duration of energy delivery. In addition, there are other factors that can limit deep lesion formation, such as early impedance rise that prevents continued energy delivery. Predicting and assessing lesion size and quality is important to the success of the ablation, but it has been difficult to achieve.

Cardiac electrical mapping (mapping the electrical activity of the heart that is associated with depolarization and/or repolarization of the myocardial tissues) and resulting electrograms (EGMs) are frequently used to locate an optimal site for ablation and/or to assess lesion formation during or after an ablation procedure. For example, electrical conduction may be reduced or eliminated in ablated tissue and, therefore, a reduction or elimination in electrical activity may indicate that sufficient lesion formation has occurred and any abnormal conduction has been blocked. However, EGMs may exaggerate or over-estimate lesion formation, and therefore may not paint an accurate picture of whether a procedure is or has been effective. An arrhythmia may return if a targeted area of tissue is not sufficiently ablated, which may necessitate re-treatment or re-ablation of the area of tissue and additional surgical procedures for the patient.

SUMMARY

The techniques of this disclosure generally relate to lesion formation assessment in tissue that has undergone one or more ablation procedures. In one embodiment, a method of assessing lesion formation comprises: recording a baseline impedance measurement from an area of tissue with a medical device; ablating the area of tissue with the medical device; recording a post-treatment impedance measurement from the area of tissue with the medical device; identifying at least one amplitude characteristic of the baseline impedance measurement and identifying at least one amplitude characteristic of the post-treatment impedance measurement; comparing the at least one amplitude characteristic of the baseline impedance measurement and the at least one amplitude characteristic of the post-treatment impedance measurement; generating an indication of efficacy based on the comparison, the indication of efficacy being one of sufficient lesion formation and insufficient lesion formation; and re-ablating the area of tissue if the indication of efficacy is insufficient lesion formation.

In one aspect of the embodiment, the at least one amplitude characteristic is a peak-to-peak amplitude.

In one aspect of the embodiment, the at least one amplitude characteristic is an average peak-to-peak amplitude over a measurement time.

In one aspect of the embodiment, the measurement time is between 1-30 seconds. In one aspect of the embodiment, the measurement time is approximately 6 seconds. In one aspect of the embodiment, the measurement time is a duration of a cardiac cycle.

In one aspect of the embodiment, the medical device includes at least one impedance sensing electrode, each of the baseline impedance measurement and the post-treatment measurement being recorded by the at least one impedance sensing electrode.

In one aspect of the embodiment, the indication of efficacy is sufficient lesion formation when the at least one impedance characteristic of the post-treatment impedance measurement is less than the at least one impedance characteristic of the baseline impedance measurement by at least a threshold amount. In one aspect of the embodiment, the indication of efficacy is sufficient lesion formation when the at least one impedance characteristic is at least one peak-to-peak amplitude and the post-treatment at least one peak-to-peak amplitude is at least 50% less than the at least one baseline peak-to-peak amplitude.

In one aspect of the embodiment, the indication of efficacy is insufficient lesion formation when the at least one impedance characteristic of the post-treatment impedance measurement is one of the same as and greater than the at least one impedance characteristic of the baseline impedance measurement by less than a threshold amount.

In one aspect of the embodiment, the medical device is part of a medical system, the medical system including a control unit, the control unit: identifying the at least one impedance characteristic of the baseline impedance measurement and identifying the at least one amplitude characteristic of the post-treatment impedance measurement; comparing the at least one amplitude characteristic of the baseline impedance measurement and the at least one amplitude characteristic of the post-treatment impedance measurement; and generating an indication of efficacy based on the comparison, the indication of efficacy being one of sufficient lesion formation and insufficient lesion formation.

In one aspect of the embodiment, the medical system is a cryoablation system.

In one aspect of the embodiment, the medical system is an electroporation system.

In one embodiment, a method of assessing lesion formation comprises: recording a baseline impedance measurement from an area of tissue with at least one impedance sensing electrode of a medical device; ablating the area of tissue with a treatment element of the medical device; recording a post-treatment impedance measurement from the area of tissue with the at least one impedance sensing electrode; identifying, with processing circuitry of a control unit that is in communication with the medical device, an average peak-to-peak amplitude of the baseline impedance measurement over time and identifying, with the processing circuitry, an average peak-to-peak amplitude of the post-treatment impedance measurement over time; comparing, with the processing circuitry, the average peak-to-peak amplitude of the baseline impedance measurement and the average peak-to-peak amplitude of the post-treatment impedance measurement; generating, with the processing circuitry, an indication of efficacy based on the comparison, the indication of efficacy being: sufficient lesion formation when the average peak-to-peak amplitude of the post-treatment impedance measurement is less than the average peak-to-peak amplitude of the baseline impedance measurement by at least a threshold amount; and insufficient lesion formation when the average peak-to-peak amplitude of the post-treatment impedance measurement is one of the same as and greater than the average peak-to-peak amplitude of the baseline impedance measurement by the threshold amount; and re-ablating the area of tissue with the treatment element if the indication of efficacy is insufficient lesion formation.

In one aspect of the embodiment, the threshold amount is approximately 50%.

In one embodiment, a medical system for asserting lesion formation comprises: a medical device having at least one impedance sensing electrode and a treatment element, the medical device being configured to ablate an area of tissue; and a control unit in communication with the medical device, the control unit including processing circuitry configured to: record a baseline impedance measurement from the area of tissue; record a post-treatment impedance measurement from the area of tissue; identify at least one amplitude characteristic of the baseline impedance measurement and identify at least one amplitude characteristic of the post-treatment impedance measurement; compare the at least one amplitude characteristic of the baseline impedance measurement and the at least one amplitude characteristic of the post-treatment impedance measurement; and generate an indication of efficacy based on the comparison, the indication of efficacy being one of sufficient lesion formation and insufficient lesion formation.

In one aspect of the embodiment, the at least one amplitude characteristic is a peak-to-peak amplitude, the indication of efficacy being: sufficient lesion formation when the peak-to-peak amplitude of the post-treatment impedance measurement is less than the peak-to-peak amplitude of the baseline impedance measurement by at least a threshold amount; and insufficient lesion formation when the peak-to-peak amplitude of the post-treatment impedance measurement is one of the same as or greater than the peak-to-peak amplitude of the baseline impedance measurement by the threshold amount. In one aspect of the embodiment, the threshold amount is approximately 50%.

In one aspect of the embodiment, the at least one amplitude characteristic is an average peak-to-peak amplitude, the indication of efficacy being: sufficient lesion formation when the average peak-to-peak amplitude of the post-treatment impedance measurement is less than the average peak-to-peak amplitude of the baseline impedance measurement by at least a threshold amount; and insufficient lesion formation when the average peak-to-peak amplitude of the post-treatment impedance measurement is one of the same as or greater than the average peak-to-peak amplitude of the baseline impedance measurement by the threshold amount. In one aspect of the embodiment, the threshold amount is approximately 50%.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

The present technology is generally related to lesion formation assessment in tissue that has undergone one or more ablation procedures. In particular, the present technology is related to using impedance measurements, in the form of peak-to-peak amplitude within the cardiac cycle, to evaluate lesion formation. The methods disclosed herein of using impedance measurements to evaluate lesion formation may be used regardless of the energy source or type of ablation procedure. For example, the methods disclosed herein may be used to evaluate whether sufficient lesion formation has occurred due to cryoablation and/or the delivery of energy such as radiofrequency energy, pulsed field ablation (PFA) energy, electroporation energy, or the like. However, cryoablation and electroporation procedures and systems are discussed herein by way of example and to provide context for the description of the lesion formation assessment methods.

Figure 1:
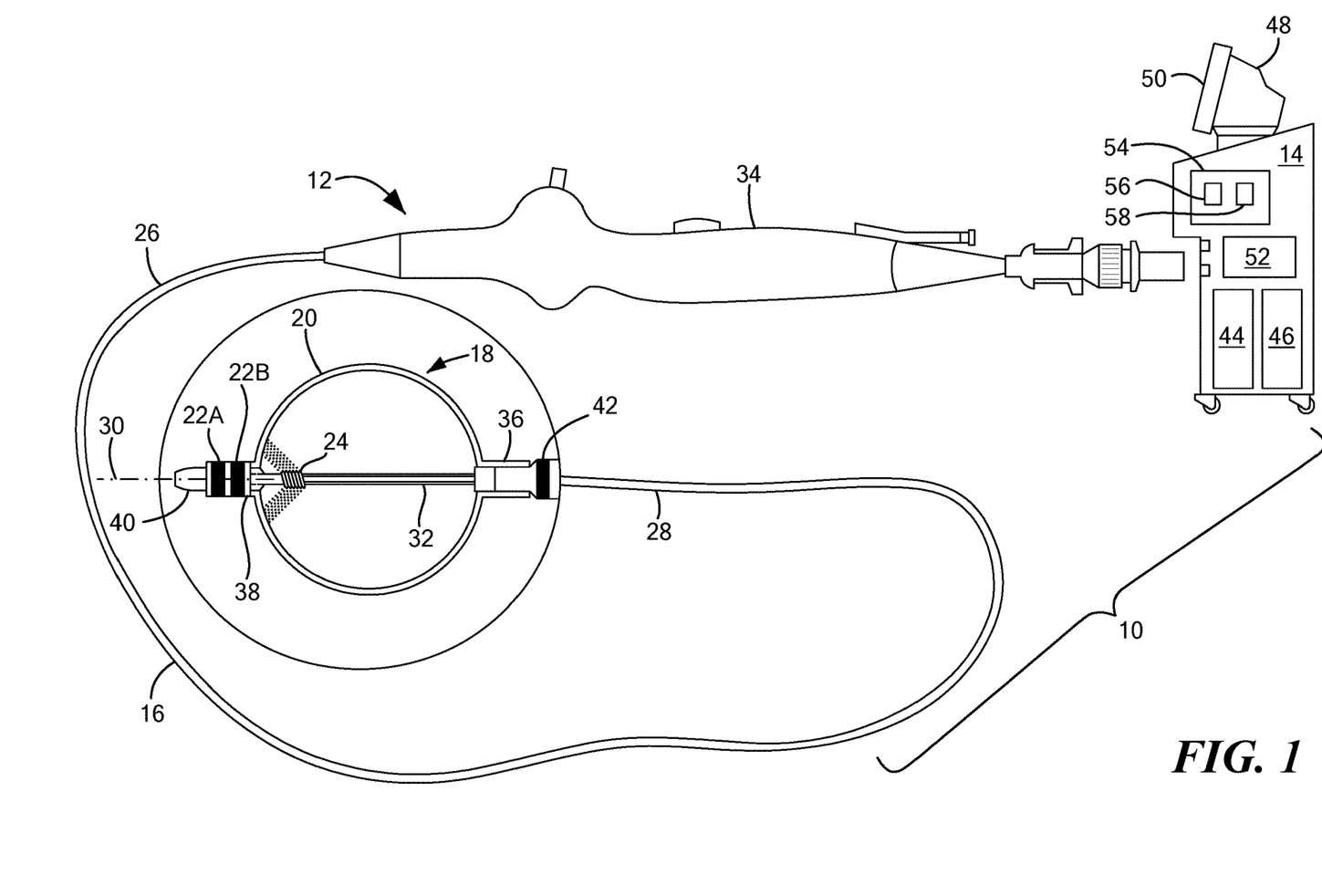
FIG. 1 is an exemplary cryoablation system configured for use in accordance with the present disclosure.

Referring now to FIG. 1, an exemplary cryoablation system configured for use in accordance with the present disclosure is shown. In one embodiment, the cryoablation system 10 generally includes a medical device 12 that is coupled or couplable to a control unit 14 or operating console. The medical device 12 may generally include one or more treatment elements for cryotherapy and, optionally, other energy modalities. In one embodiment, the medical device 12 is a cryoablation device that generally includes an elongate body 16 and one or more diagnostic or treatment elements 18 for energetic, therapeutic, and/or investigatory interaction between the medical device 12 and an area of tissue (such as a treatment site). In one embodiment, the treatment element 18 includes a balloon 20, at least one impedance sensing electrode 22, and at least one coolant injection element 24.

Continuing to refer to FIG. 1, in one embodiment the elongate body 16 is passable through a patient's vasculature and/or proximate to a tissue region for diagnosis or treatment, and may be a catheter, sheath, intravascular introducer, or the like. In one embodiment, the elongate body 16 includes a proximal portion 26, a distal portion 28 opposite the proximal portion 26, a longitudinal axis 30, and one or more lumens or conduits 32 disposed within the elongate body 16 and/or the treatment element 18 that provide mechanical, electrical, and/or fluid communication between the proximal portion 26 and the distal portion 28 of the elongate body 16. In one embodiment, the proximal portion 26 of the elongate body 16 is coupled to a handle 34 having one or more knobs, levers, connectors, umbilicals, and/or other components used for steering, manipulating, and operating the medical device 12 and connecting the medical device 12 to the control unit 14.

Continuing to refer to FIG. 1, in one embodiment the treatment element 18 is located at or within the distal portion 28 of the elongate body 16 and includes at least one impedance sensing electrode 22. In the exemplary system shown in FIG. 1, for example, the treatment element 18 includes a balloon 20 having a proximal neck 36 and a distal neck 38. The proximal neck 36 may be coupled to (for example, adhered with a biocompatible adhesive or bonded to) the distal portion 28 of the elongate body 16, and the distal neck 38 may be coupled to (as is the proximal neck 36) the distal portion 28 of the elongate body 16 and/or to a distal portion 40 of a shaft or guide wire lumen 32 that extends from the elongate body 16. However, it will be understood that the balloon 20 may be coupled to the distal end 29 of the elongate body 16 in any manner that allows for inflation of the balloon 20 without leaking coolant into the patient's body. Further, although not shown, the treatment element 18 may include a second balloon disposed on the outside or inside of the first balloon to offer additional protection against leaks and tears. Additionally, the balloon 20 may further include one or more layers providing for puncture resistance, radiopacity, or the like, and may also be substantially electrically insulative.

Continuing to refer to FIG. 1, in one embodiment each of the at least one impedance sensing electrode 22 is composed of electrically conductive material (such as metal) and is configured to convey an electrical signal, current, and/or voltage to a designated area of tissue and/or for measuring, recording, or otherwise assessing one or more electrical properties or characteristics of surrounding tissue. The impedance sensing electrodes 22 (and any other electrodes of the medical device 12) may be configured in a myriad of different geometric configurations or controllably deployable shapes, and may also vary in number to suit a particular application, targeted tissue structure or physiological feature. For example, in one embodiment the at least one impedance sensing electrode 22 includes two impedance sensing electrodes 22 that are located distal to the balloon 20 and are coupled to the distal neck 38 of the balloon 20. In one embodiment, the medical device 12 includes a first impedance sensing electrode 22A located distal to the balloon 20 and a second impedance sensing electrode 22B located proximal to the first impedance sensing electrode 22A and distal to the balloon 20. However, it will be understood that the impedance sensing electrode(s) 22 may be at any location on the medical device 12 that allows or facilitates their contact with a target area of tissue and impedance measurement from that target area of tissue. Further, the at least one impedance sensing electrode 22 may include one impedance sensing electrode or more than one impedance sensing electrode, such as an impedance sensing electrode array disposed on the balloon 20. Each impedance sensing electrode 22 is configured to record impedance and, in some embodiments, may also be configured to record temperature and/or other characteristics from tissue and/or blood that is in contact with or proximate the impedance sensing electrode 22. In one embodiment, the medical device 12 also includes at least one reference electrode 42. Further, it will be understood that FIG. 1 shows a non-limiting example of a medical system and that other device and/or impedance sensing electrode configurations are contemplated that allow impedance measurements to be recorded from an area of tissue.

Continuing to refer to FIG. 1, in one embodiment the control unit 14 is in fluid and electrical communication with the medical device 12 and includes one or more fluid (for example, cryotreatment coolant) source reservoirs 44, fluid recovery reservoirs 46, computers 48 with displays 50, and may further include various other displays, screens, user input controls, keyboards, buttons, valves, conduits, sensors, connectors, power sources, energy generators, processors, and computers for adjusting and monitoring system parameters. For example, in one embodiment the cryoablation system 10 also includes an energy generator 52, which may be located in or as part of the control unit 14. In one embodiment, the impedance sensing electrode(s) 22 are electrical communication with the energy generator 52 for the application of energy to the impedance sensing electrode(s) 22 for sensing impedance and, optionally, for mapping cardiac electrograms from adjacent tissue. As used herein, the term "computer" may refer to any programmable data-processing unit, including a smart phone, dedicated internal circuitry, user control device, or the like.

Continuing to refer to FIG. 1, in one embodiment the computer 48 includes processing circuitry 54 having a processor 56 and a memory 58. The memory 58 is in electrical communication with the processor 56 and has instructions that, when executed by the processor 56, configure the processor 56 to execute at least one algorithm for analyzing impedance measurements recorded by the impedance sensing electrode(s) 22, assessing lesion formation in an area of tissue, for generating one or more displays or alerts to notify the user of various system criteria or determinations, and/or providing other system functionality. In one embodiment, the processing circuitry 54 is in electrical communication with the impedance sensing electrode(s) 22, the reference electrode(s) 42, the treatment element(s) 18, and/or other components of the system 10. In one embodiment, the processing circuitry 54 includes an impedance measurement module or signal processing unit to measure one or more impedance characteristics (such as magnitude and/or phase) between the impedance sensing electrodes 22 and/or between the impedance sensing electrode(s) and the reference electrode 42. For example, an excitation current may be applied (such as from the energy generator 52) between one or more of the impedance sensing electrodes 22 and/or an energy return electrode, and the resulting impedance is measured. In some embodiments, excitation and the resulting measurements for impedance parameters may continue or otherwise be repeated until impedance measurements are calculated for various combinations of impedance sensing electrodes 22 before, during, and/or after the delivery of, for example, cryotherapy or electroporation.

As used herein, the term "impedance" refers to the generally accepted definition of the term: a complex ratio of sinusoidal voltage to current in an electric circuit or component, except that as used herein, impedance shall apply to any region or space through which some electrical field is applied and current flows. The impedance, Z, may be expressed as a complex number, $Z=R+jX$, wherein R is the resistance in real number ohms, X is the reactance in imaginary ohms, and j is a multiplier that is the positive square root of negative one (−1). Impedance may also be expressed in polar form as $Z=|Z|e^{j\theta}$, where $|Z|$ is the magnitude (e.g., the ratio of the voltage difference amplitude to the current amplitude), θ is the phase difference between voltage and current, and j is the imaginary unit.

Figure 2:
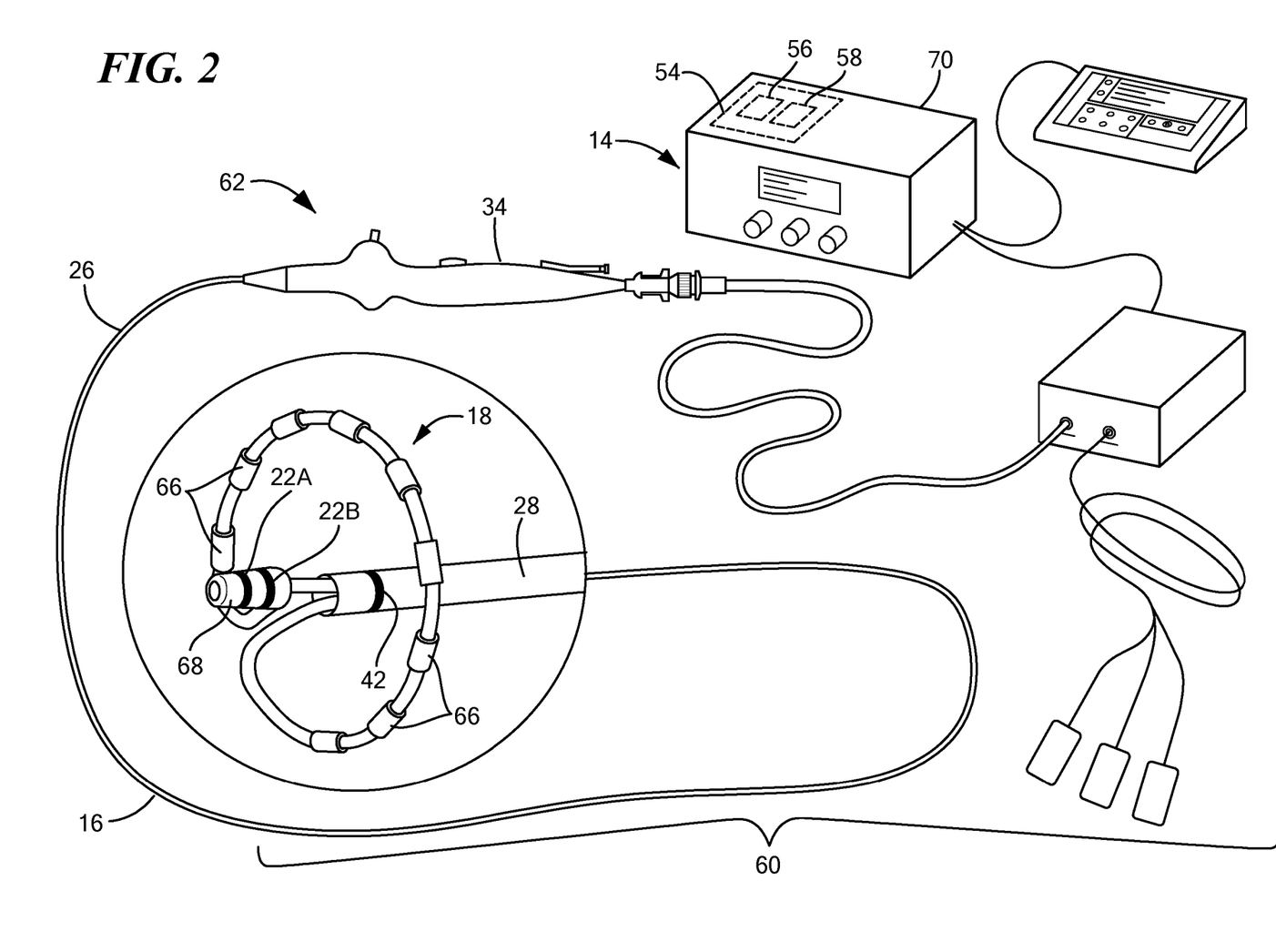
FIG. 2 is an exemplary ablation system including an electrosurgical generator and medical device for delivering at least one of radiofrequency energy, pulsed field ablation energy, and electroporation energy, the ablation system being configured for use in accordance with the present disclosure.

Referring now to FIG. 2, an exemplary ablation system including an electrosurgical generator and medical device for delivering at least one of radiofrequency energy, pulsed field ablation energy, and electroporation energy is shown. In some embodiments, many components of the electrosurgical system 60 are functionally equivalent to components of the cryoablation system 10 shown in FIG. 1 and, as such, will be designated with like reference numbers and not discussed in detail regarding FIG. 2.

Continuing to refer to FIG. 2, in one embodiment the medical device 62 is an electroporation device and the treatment element 18 includes an electrode array with a plurality of treatment electrodes 66 that are configured to deliver energy to an area of tissue, such as electroporation energy (and/or radiofrequency energy, pulsed field ablation energy, or the like). However, it will be understood that the treatment element 18 may have any suitable size, shape, or configuration and is not limited to the configuration shown in FIG. 2. For example, the treatment element 18 may be an expandable element such as a balloon having one or more treatment electrodes 66 on an outer surface of the balloon. Like the medical device 12 of FIG. 1, however, the medical device 62 of FIG. 2 includes at least one impedance sensing electrode 22. In one embodiment, the medical device 12 includes two impedance sensing electrodes 22 that are located approximately in the same plane as or distal to the treatment element 18, such as on a distal tip 68 of the medical device 62. However, it will be understood that the impedance sensing electrode(s) 22 may be at any location on the medical device 62 that allows or facilitates their contact with a target area of tissue and impedance measurement from that target area of tissue. Further, the at least one impedance sensing electrode 22 may include one impedance sensing electrode or more than one impedance sensing electrode, such as a plurality of impedance sensing electrodes located on the treatment element 18. Each impedance sensing electrode 22 is configured to record impedance and, in some embodiments, may also be configured to record temperature and/or other characteristics from tissue and/or blood that is in contact with or proximate the impedance sensing electrode 22. In one embodiment, the medical device 62 also includes at least one reference electrode 42. Further, it will be understood that FIG. 2 shows a non-limiting example of a medical system and that other device and/or impedance sensing electrode configurations are contemplated that allow impedance measurements to be recorded from an area of tissue.

Continuing to refer to FIG. 2, in one embodiment the control unit 14 is in electrical communication with the medical device 62 and includes one or more electroporation energy generators 70, computers 48 with displays 50, and may further include various other displays, screens, user input controls, keyboards, buttons, valves, conduits, sensors, connectors, power sources, energy generators, processors, and computers for adjusting and monitoring system parameters. In one embodiment the energy generator 70 is in electrical communication with the treatment electrodes 66, the impedance sensing electrode(s) 22, and the reference electrode 42 for the delivery of energy from the treatment electrodes 66 to an area of tissue and for the application of energy to the impedance sensing electrode(s) 22 for sensing impedance and, optionally, for mapping cardiac electrograms from adjacent tissue. In other embodiments, the electrosurgical system 60 may also include a separate energy generator (not shown) that is in electrical communication with the impedance sensing electrode(s) 22 and/or the reference electrode 42 only, with the treatment electrodes 66 being in communication with the energy generator 70 as a primary treatment energy source. The electrosurgical system 60 may be configured to deliver energy in unipolar, bipolar, and/or combination unipolar/bipolar mode. If configured to delivery energy in unipolar or combination unipolar/bipolar mode, the electrosurgical system 60 may further include an energy return electrode (not shown) attached to the patient's skin. Further, in one embodiment the processing circuitry 54 of the electrosurgical system 60 is as described regarding the cryoablation system of FIG. 1.

Figure 3:
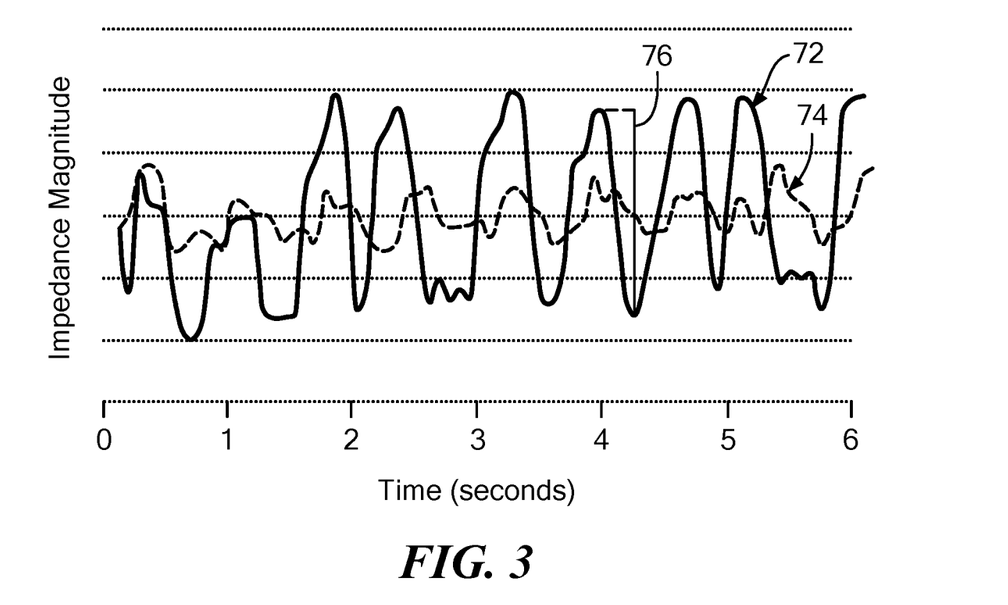
FIG. 3 is an exemplary chart showing impedance measured from an area of tissue over time before and after cryoablation of the area of tissue.
Figure 4:
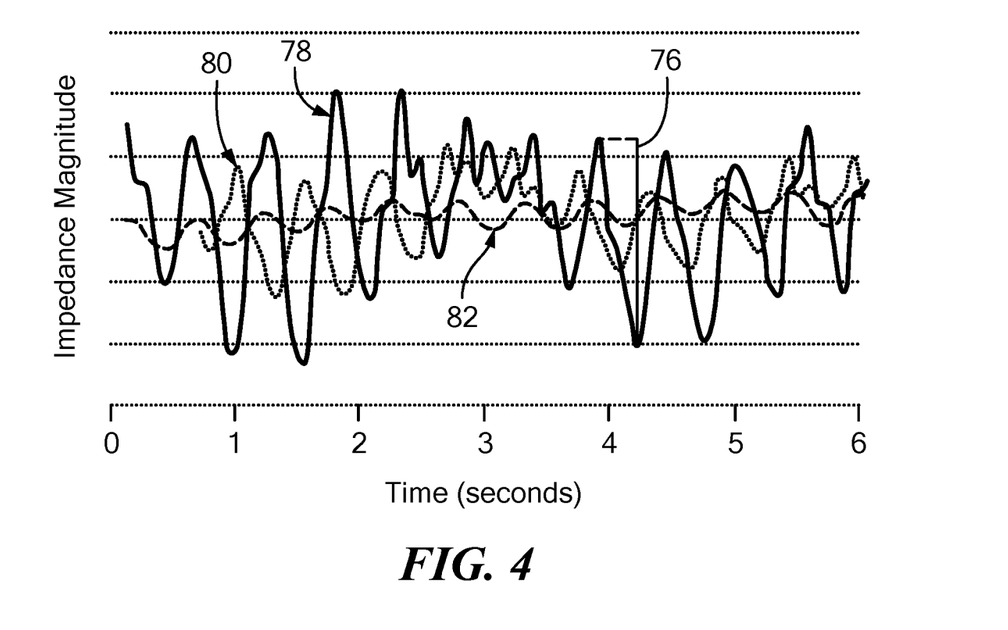
FIG. 4 is an exemplary chart showing impedance measured from an area of tissue over time before the delivery of electroporation energy to the area of tissue, after the delivery of a low dose of electroporation energy, and after the delivery of a high dose of electroporation energy.

Referring now to FIGS. 3 and 4, exemplary charts showing impedance measured from an area of tissue before, during, and/or after an ablation procedure are shown. FIG. 3 shows impedance measured from an area of tissue over time before and after cryoablation of the area of tissue and FIG. 4 shows impedance measured from an area of tissue over time before the delivery of electroporation energy, after the delivery of a low dose of electroporation energy, and after the delivery of a high dose of electroporation energy. Of note, the impedance values shown in FIGS. 3 and 4 are zeroed impedance magnitude, meaning that the mean value of the impedance measured from the area of tissue has been shifted to 0. Further, the impedance values shown in FIGS. 3 and 4 were acquired over multiple cardiac cycles.

Referring now to the exemplary data shown in FIG. 3, a magnitude of impedance measured by the impedance sensing electrode(s) 22 from an area of tissue before a cryoablation procedure (line 72) is greater than a magnitude of impedance measured by the impedance sensing electrode(s) 22 from the same area of tissue after the completion of the cryoablation procedure (line 74). Likewise, FIG. 3 shows that the peak-to-peak amplitudes (which may be referred to herein as p-p amplitude) 76 along line 72 is greater than the p-p amplitudes along line 74 and, therefore, the average p-p amplitude of the impedance measured before a cryoablation procedure (line 72) is greater than the average p-p amplitude of the impedance measured after the completion of the cryoablation procedure (line 74). As tissue impedance decreases as the tissue is ablated, such post-ablation impedance measurements, including p-p amplitude, is indicative that adequate lesion formation has occurred. For example, in one embodiment the processing circuitry 54 is configured to use absolute p-p amplitudes, average p-p amplitudes, absolute difference(s) in pre- and post-ablation amplitudes, percentage difference(s) in pre- and post-ablation amplitudes, and/or change in p-p amplitude(s) over time to determine whether sufficient lesion formation has occurred in the measured area of tissue. In one embodiment, a reduction of more than approximately 50% (±5%) in p-p amplitude, or a reduction of more than approximately 50% (±5%) in average p-p amplitude over time, is indicative of significant and sufficient tissue death across ablation modalities (cryoablation, radiofrequency ablation, electroporation, or the like). Impedance values, or ranges of impedance values, that are indicative of sufficient lesion formation may depend on electrode size, material, and spacing, tissue type, energy source, and/or other parameters. In one embodiment, the processing circuitry 54 is also configured to generate a signal to the user (for example, a displayed text, audio, visual, or other signal) to alert the user if sufficient lesion formation has occurred, and no repeat ablation in a given area of tissue is required, or if sufficient lesion formation has not occurred, and it is recommended that the user repeat the ablation procedure at that area of tissue.

Referring now to the exemplary data shown in FIG. 4, a magnitude of impedance measured by the impedance sensing electrode(s) 22 from an area of tissue before the delivery of electroporation energy (line 78) is greater than a magnitude of impedance measured by the impedance sensing electrode(s) 22 from the same area of tissue after either the delivery of a low dose of electroporation energy (line 80) or after the delivery of a high dose of electroporation energy (line 82). Further, FIG. 4 shows that the magnitude of impedance measured by the impedance sensing electrode(s) 22 from the area of tissue after the delivery of a low dose of electroporation energy (line 80) is greater than the magnitude of the impedance measured by the impedance sensing electrode(s) 22 from the area of tissue after the delivery of a high dose of electroporation energy (line 82). Likewise, FIG. 4 shows that the p-p amplitudes 76 along line 78 is greater than the p-p amplitudes along either of lines 80 and 82 and, therefore, the average p-p amplitude of the impedance measured before an electroporation procedure (line 78) is greater than the average p-p amplitude of the impedance measured after the completion of the electroporation procedure (using either low dose (line 80) of high dose (line 82) of electroporation energy). Further, FIG. 4 shows that, based on at least p-p amplitude, the delivery of a high dose of electroporation energy (line 82) is more effective for lesion formation, at least over a certain period of time, than is the delivery of a low dose of electroporation energy (line 80). The dosage (for example, voltage and/or voltage over time) of electroporation energy may vary based on the device used to deliver the energy, the type of tissue to which the energy is delivered, or the like. However, the high dose in a given procedure or type of procedure is greater than the low does in the same procedure or type of procedure. As tissue impedance decreases as the tissue is ablated, such post-ablation impedance measurements is indicative that adequate lesion formation has occurred. For example, in one embodiment the processing circuitry 54 is configured to use absolute p-p amplitudes, average p-p amplitudes, absolute difference(s) in pre- and post-ablation amplitudes, percentage difference(s) in pre- and post-ablation amplitudes, and/or change in p-p amplitude(s) over time to determine whether sufficient lesion formation has occurred in the measured area of tissue. In one embodiment, the processing circuitry 54 is also configured to generate a signal to the user (for example, a displayed text, audio, visual, or other signal) to alert the user if sufficient lesion formation has occurred, and no repeat ablation in a given area of tissue is required, or if sufficient lesion formation has not occurred, and it is recommended that the user repeat the ablation procedure at that area of tissue.

Figure 5:
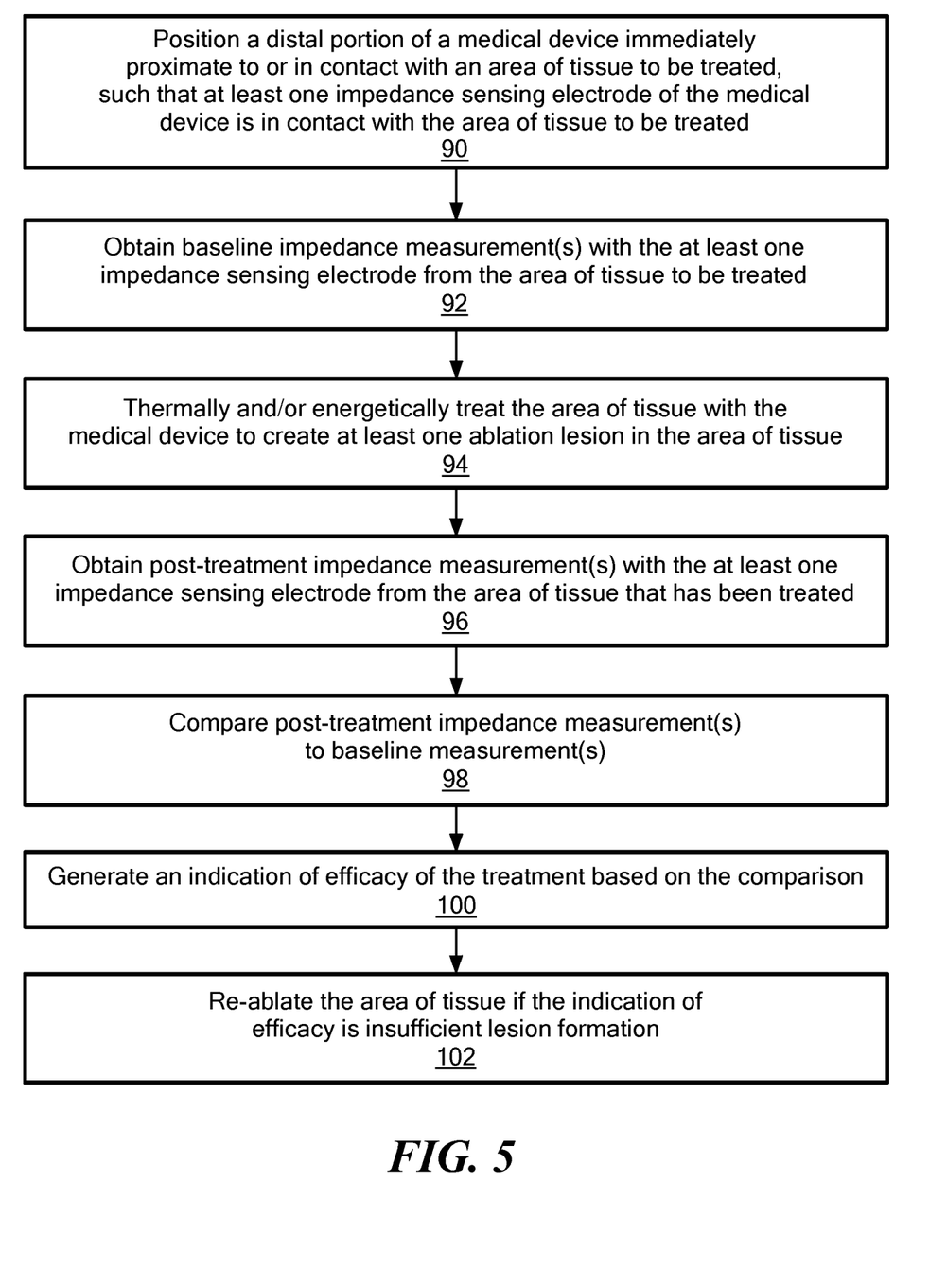
FIG. 5 is a flow chart showing an exemplary method of assessing lesion formation in accordance with the present disclosure.

Referring now to FIG. 5, a flow chart showing an exemplary method of assessing lesion formation is shown. In an exemplary method of use, the system 10, 60 may be used to treat tissue and to assess the resulting efficacy of the treatment. In particular, the medical device 12 may be used to assess contact with the targeted area of tissue, thermally treat tissue using cryogenic, electroporation, and/or radiofrequency energy (and/or other energy modalities) provided by the control unit 14, and then provide measurements or indications of the efficacy of the treatment. The thermal treatment may include ablating one or more portions of a targeted area of tissue or region, such as in the heart. Before, during and after completion of the desired thermal treatment, the medical device 12 and control unit 14 may be used to assess one or more characteristics of the treated areas of tissue. The impedance sensing electrode(s) 22 of the medical device 12 may be used to measure one or more impedance characteristics of the treated area of tissue as an indication of the rate of tissue treatment, treatment continuity, and/or treatment depth (that is, the sufficiency of lesion formation). The measured characteristics may further be used post-treatment in a secondary or follow-up procedure to locate and assess previously treated tissue regions.

Continuing to refer to FIG. 5, in a first step 90 in one embodiment, the distal portion 28 and/or the treatment element 18 of the medical device 12 may be positioned immediately proximate to or in contact with an area of tissue or structure to be treated, such that at least one impedance sensing electrode 22 is positioned in contact with the targeted area of tissue.

Continuing to refer to FIG. 5, in a second step 92 in one embodiment, the impedance sensing electrode(s) 22 are used to assess or record a first series of one or more impedance characteristics over time (that is, to measure a first series of impedance measurements) once the medical device 12 is in a desired position. In one embodiment, the first series of impedance measurements is used to establish a pre-procedure baseline (which may be referred to herein as baseline impedance measurements) and/or to assess the contact between the medical device 12 and the area of tissue. In one embodiment, the impedance measurements are taken with the impedance sensing electrodes(s) 22 of the medical device 12 and processed by one or more components of the control unit, such as the processing circuitry 54. Further, in one embodiment the processing circuitry 54 identifies at least one amplitude characteristic of the baseline impedance measurements. In one embodiment, the processing circuitry 54 identifies peak-to-peak (p-p) amplitudes and, in some embodiments, calculates an average p-p amplitude over the period of time over which the baseline impedance measurements are taken (which may be referred to herein as the baseline measurement time). The baseline measurement time may be, for example, between 1-30 seconds, between 2-15 seconds, between 5-10 seconds, or approximately 6 seconds (±0.5 second). In one embodiment, the baseline measurements are taken over at least one cardiac cycle (that is, a period of time beginning with contraction of the atria and ending with ventricular relaxation), for example, at least approximately 0.8 second. The first series of impedance measurements may be taken using a single polarity (for example, monopolar or bipolar), at a single frequency, or may include both multi-polarity and multi-frequency measurements and combinations thereof. In one non-limiting example, an excitation frequency is between 10 Hz and 20 Hz. In another non-limiting example, an excitation frequency is between 10 kHz and 800 kHz. Of note, the measurements described herein may be obtained through direct sensing or measuring of a property or characteristic (e.g., impedance, resistance, etc.) between two or more electrodes, or may be obtained through calculations derived from a subset or direct measurements. For example, to obtain multiple impedance measurements between various combinations of existing electrodes, a plurality of bipolar and unipolar measurements may be taken, while calculating remaining values between other combinations of electrodes using matrix math or other computational algorithm.

Optionally, the baseline impedance measurements may be used to evaluate contact between the medical device 12 and the area of tissue.

Continuing to refer to FIG. 5, in a third step 94 in one embodiment, the medical device is used to thermally and/or energetically treat the targeted area of tissue area to create at least one ablation lesion once the baseline impedance measurements have been recorded. Put another way, the medical device 12 is used to ablate the area of tissue. The thermal and/or energetic treatment may include, for example, circulating a coolant from the control unit 14 to the treatment element 18, such as a balloon 20, of the medical device 12 in a system 10 configured for cryoablation (for example, as shown in FIG. 1) and/or transmitting electroporation energy from an energy generator 70 to the treatment element 18, such as a plurality of treatment electrodes 66, of the medical device 12 in a system 60 configured for electroporation (for example, as shown in FIG. 2), or using other thermal and/or energetic modalities, or combinations thereof.

Continuing to refer to FIG. 5, in a fourth step 96 in one embodiment, the impedance sensing electrode(s) 22 are used to assess or record a second series of one or more post-treatment impedance characteristics over time (that is, to measure a second series of impedance measurements) upon completion of the treatment procedure. The post-treatment impedance measurements may include impedance characteristics taken with similar parameters to the baseline impedance measurements described above. In one embodiment, the post-treatment impedance measurements are taken after the delivery of cryotherapy (for example, as shown in FIG. 3). In one embodiment, the post-treatment impedance measurements are taken after the delivery of a low dose of electroporation energy and/or after the delivery of a high dose of electroporation energy (for example, as shown in FIG. 4). Further, in one embodiment the processing circuitry 54 identifies at least one amplitude characteristic of the post-treatment impedance measurements. In one embodiment, the processing circuitry 54 identifies peak-to-peak (p-p) amplitudes and, in some embodiments, calculates an average p-p amplitude over the time over which the post-treatment impedance measurements are taken (which may be referred to herein as the post-treatment measurement time). The post-treatment measurement time may be, for example, between 1-30 seconds, between 2-15 seconds, between 5-10 seconds, or approximately 6 seconds (±0.5 second). In one embodiment, the baseline measurements are taken over at least one cardiac cycle (that is, a period of time beginning with contraction of the atria and ending with ventricular relaxation), for example, approximately 0.8 second.

Continuing to refer to FIG. 5, in a fifth step 98 in one embodiment, the post-treatment impedance measurements are compared to the baseline measurements to create an indication of the efficacy of the treatment on the targeted area of tissue, or the post-treatment measurements may be used on their own to determine the resulting characteristics of the treated area of tissue, such as lesion depth and/or continuity. In one embodiment, comparing the baseline and post-treatment measurements includes comparing at least one amplitude characteristic of the baseline measurements to at least one amplitude characteristic of the post-treatment measurements. Comparing the baseline to the post-treatment impedance measurements may include, for example, comparing absolute p-p amplitudes, comparing average p-p amplitudes, comparing absolute difference(s) in pre- and post-ablation amplitudes, comparing percentage difference(s) in pre- and post-ablation amplitudes, and/or comparing change in p-p amplitude(s) over time. Additionally or alternatively, the post-treatment impedance measurements may be compared to pre-established thresholds or values to determine whether the impedance values indicate a continuity and/or sufficient lesion depth in the thermally treated or ablated lesion.

Continuing to refer to FIG. 5, in a sixth step 100 in one embodiment, the processing circuitry 54 generates an indication of the efficacy of the treatment based on the comparison between the post-treatment impedance measurements and the baseline impedance measurements and/or predetermined, pre-established thresholds or values indicating efficacy. For example, the indication of efficacy may be one of sufficient lesion formation and insufficient lesion formation. In one embodiment, the processing circuitry 54 generates a user alert or indication of the analysis (for example, a displayed text, audio, visual, or other signal) based on the indication of the efficacy of the treatment. For example, if the processing circuitry 54 determines that a p-p amplitude or average of p-p amplitudes of the post-treatment impedance measurements differs by a threshold absolute and/or percentage amount (or range thereof), the processing circuitry 54 may then generate an alert to communicate to the user that the treatment has resulted in sufficient lesion formation and no further treatment is required at that area of tissue. Conversely, if the processing circuitry 54 determines that a p-p amplitude or average of p-p amplitudes of the post-treatment impedance measurements does not differ by a threshold absolute and/or percentage amount (or range thereof), the processing circuitry 54 may then generate an alert to communicate to the user that the treatment has not resulted in sufficient lesion formation and further treatment is required or recommended at that area of tissue. Thus, in a seventh step 102 in one embodiment, a user may re-ablate the area of tissue if the indication of efficacy is insufficient lesion formation. Likewise, the user may end the procedure (that is, not perform a further ablation of the area of tissue) if the indication of efficacy is sufficient lesion formation. For example, this may enable the user to sufficiently ablate the area of tissue during one procedure, rather than risking an arrhythmia returns to the area of tissue, as may be the case if the lesion(s) are insufficiently formed, which would require the patient to undergo a second or subsequent procedures.

Embodiments

In one embodiment, a method of assessing lesion formation comprises: recording a baseline impedance measurement from an area of tissue with a medical device 12; ablating the area of tissue with the medical device 12; recording a post-treatment impedance measurement from the area of tissue with the medical device 12; identifying at least one amplitude characteristic of the baseline impedance measurement and identifying at least one amplitude characteristic of the post-treatment impedance measurement; comparing the at least one amplitude characteristic of the baseline impedance measurement and the at least one amplitude characteristic of the post-treatment impedance measurement; generating an indication of efficacy based on the comparison, the indication of efficacy being one of sufficient lesion formation and insufficient lesion formation; and re-ablating the area of tissue if the indication of efficacy is insufficient lesion formation.

In one aspect of the embodiment, the at least one amplitude characteristic is a peak-to-peak amplitude 76.

In one aspect of the embodiment, the at least one amplitude characteristic is an average peak-to-peak amplitude over a measurement time.

In one aspect of the embodiment, the measurement time is between 1-30 seconds. In one aspect of the embodiment, the measurement time is approximately 6 seconds. In one aspect of the embodiment, the measurement time is a duration of a cardiac cycle.

In one aspect of the embodiment, the medical device 12 includes at least one impedance sensing electrode 22, each of the baseline impedance measurement and the post-treatment measurement being recorded by the at least one impedance sensing electrode 22.

In one aspect of the embodiment, the indication of efficacy is sufficient lesion formation when the at least one impedance characteristic of the post-treatment impedance measurement is less than the at least one impedance characteristic of the baseline impedance measurement by at least a threshold amount. In one aspect of the embodiment, the indication of efficacy is sufficient lesion formation when the at least one impedance characteristic is at least one peak-to-peak amplitude and the post-treatment at least one peak-to-peak amplitude is at least 50% less than the at least one baseline peak-to-peak amplitude.

In one aspect of the embodiment, the indication of efficacy is insufficient lesion formation when the at least one impedance characteristic of the post-treatment impedance measurement is one of the same as and greater than the at least one impedance characteristic of the baseline impedance measurement by less than a threshold amount.

In one aspect of the embodiment, the medical device 12 is part of a medical system 10, 60, the medical system 10, 60 including a control unit 14, the control unit 14: identifying the at least one impedance characteristic of the baseline impedance measurement and identifying the at least one amplitude characteristic of the post-treatment impedance measurement; comparing the at least one amplitude characteristic of the baseline impedance measurement and the at least one amplitude characteristic of the post-treatment impedance measurement; and generating an indication of efficacy based on the comparison, the indication of efficacy being one of sufficient lesion formation and insufficient lesion formation.

In one aspect of the embodiment, the medical system 10 is a cryoablation system.

In one aspect of the embodiment, the medical system 60 is an electroporation system.

In one embodiment, a method of assessing lesion formation comprises: recording a baseline impedance measurement from an area of tissue with at least one impedance sensing electrode 22 of a medical device 12; ablating the area of tissue with a treatment element 18 of the medical device 12; recording a post-treatment impedance measurement from the area of tissue with the at least one impedance sensing electrode 22; identifying, with processing circuitry 54 of a control unit 14 that is in communication with the medical device 12, an average peak-to-peak amplitude of the baseline impedance measurement over time and identifying, with the processing circuitry 54, an average peak-to-peak amplitude of the post-treatment impedance measurement over time; comparing, with the processing circuitry 54, the average peak-to-peak amplitude of the baseline impedance measurement and the average peak-to-peak amplitude of the post-treatment impedance measurement; generating, with the processing circuitry 54, an indication of efficacy based on the comparison, the indication of efficacy being: sufficient lesion formation when the average peak-to-peak amplitude of the post-treatment impedance measurement is less than the average peak-to-peak amplitude of the baseline impedance measurement by at least a threshold amount; and insufficient lesion formation when the average peak-to-peak amplitude of the post-treatment impedance measurement is one of the same as and greater than the average peak-to-peak amplitude of the baseline impedance measurement by the threshold amount; and re-ablating the area of tissue with the treatment element 18 if the indication of efficacy is insufficient lesion formation.

In one aspect of the embodiment, the threshold amount is approximately 50%.

In one embodiment, a medical system 10, 60 for asserting lesion formation comprises: a medical device 12 having at least one impedance sensing electrode 22 and a treatment element 18, the medical device 12 being configured to ablate an area of tissue; and a control unit 14 in communication with the medical device 12, the control unit 14 including processing circuitry 54 configured to: record a baseline impedance measurement from the area of tissue; record a post-treatment impedance measurement from the area of tissue; identify at least one amplitude characteristic of the baseline impedance measurement and identify at least one amplitude characteristic of the post-treatment impedance measurement; compare the at least one amplitude characteristic of the baseline impedance measurement and the at least one amplitude characteristic of the post-treatment impedance measurement; and generate an indication of efficacy based on the comparison, the indication of efficacy being one of sufficient lesion formation and insufficient lesion formation.

In one aspect of the embodiment, the at least one amplitude characteristic is a peak-to-peak amplitude, the indication of efficacy being: sufficient lesion formation when the peak-to-peak amplitude of the post-treatment impedance measurement is less than the peak-to-peak amplitude of the baseline impedance measurement by at least a threshold amount; and insufficient lesion formation when the peak-to-peak amplitude of the post-treatment impedance measurement is one of the same as or greater than the peak-to-peak amplitude of the baseline impedance measurement by the threshold amount. In one aspect of the embodiment, the threshold amount is approximately 50%.

In one aspect of the embodiment, the at least one amplitude characteristic is an average peak-to-peak amplitude, the indication of efficacy being: sufficient lesion formation when the average peak-to-peak amplitude of the post-treatment impedance measurement is less than the average peak-to-peak amplitude of the baseline impedance measurement by at least a threshold amount; and insufficient lesion formation when the average peak-to-peak amplitude of the post-treatment impedance measurement is one of the same as or greater than the average peak-to-peak amplitude of the baseline impedance measurement by the threshold amount. In one aspect of the embodiment, the threshold amount is approximately 50%.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of assessing lesion formation, the method comprising:
   recording a baseline impedance measurement from an area of tissue with a medical device;
   ablating the area of tissue with the medical device;
   recording a post-treatment impedance measurement from the area of tissue with the medical device after completion of ablating the area of tissue;
   identifying at least one amplitude characteristic of the baseline impedance measurement and identifying at least one amplitude characteristic of the post-treatment impedance measurement;
   comparing the at least one amplitude characteristic of the baseline impedance measurement and the at least one amplitude characteristic of the post-treatment impedance measurement;
   generating an indication of efficacy based on the comparison and providing the indication of efficacy to a display, the indication of efficacy being one of sufficient lesion formation and insufficient lesion formation; and
   re-ablating the area of tissue if the indication of efficacy is insufficient lesion formation.

2. The method of claim 1, wherein the at least one amplitude characteristic of the baseline impedance measurement is a peak-to-peak amplitude, and wherein the at least one amplitude characteristic of the post-treatment impedance measurement is a peak-to-peak amplitude.

3. The method of claim 1, wherein the at least one amplitude characteristic of the baseline impedance measurement is an average peak-to-peak amplitude over a measurement time, and wherein the at least one amplitude characteristic of the post-treatment impedance measurement is an average peak-to-peak amplitude over a measurement time.

4. The method of claim 3, wherein the measurement time is between 1-30 seconds.

5. The method of claim 3, wherein the measurement time is approximately 6 seconds.

6. The method of claim 3, wherein the measurement time is a duration of a cardiac cycle.

7. The method of claim 1, wherein the medical device includes at least one impedance sensing electrode, each of the baseline impedance measurement and the post-treatment impedance measurement being recorded by the at least one impedance sensing electrode.

8. The method of claim 1, wherein the indication of efficacy is sufficient lesion formation when the at least one amplitude characteristic of the post-treatment impedance measurement is less than at least one impedance characteristic of the baseline impedance measurement by at least a threshold amount.

9. The method of claim 8, wherein the indication of efficacy is sufficient lesion formation when the at least one impedance characteristic of the baseline impedance measurement is at least one peak-to-peak amplitude, at least one impedance characteristic of the post-treatment impedance measurement is at least one peak-to-peak amplitude, and the post-treatment at least one peak-to-peak amplitude is at least 50% less than the at least one baseline peak-to-peak amplitude.

10. The method of claim 1, wherein the indication of efficacy is insufficient lesion formation when the at least one impedance characteristic of the post-treatment impedance measurement is the same as at least one impedance characteristic of the baseline impedance measurement, or the at least one impedance characteristic of the post-treatment impedance measurement is greater than the at least one impedance characteristic of the baseline impedance measurement by less than a threshold amount.

11. The method of claim 1, wherein the medical device is part of a medical system, the medical system including a control unit, the control unit:
    identifying at least one impedance characteristic of the baseline impedance measurement and identifying the at least one amplitude characteristic of the post-treatment impedance measurement;
    comparing the at least one amplitude characteristic of the baseline impedance measurement and the at least one amplitude characteristic of the post-treatment impedance measurement; and
    generating an indication of efficacy based on the comparison, the indication of efficacy being one of sufficient lesion formation and insufficient lesion formation.

12. The method of claim 11, wherein the medical system is a cryoablation system.

13. The method of claim 11, wherein the medical system is an electroporation system.

14. A method of assessing lesion formation, the method comprising:
    record a baseline impedance measurement from an area of tissue with at least one impedance sensing electrode of a medical device;
    ablating the area of tissue with a treatment element of the medical device;
    recording a post-treatment impedance measurement from the area of tissue with the at least one impedance sensing electrode after completion of ablating the area of tissue;

identifying, with processing circuitry of a control unit that is in communication with the medical device, an average peak-to-peak amplitude of the baseline impedance measurement over time and identifying, with the processing circuitry, an average peak-to-peak amplitude of the post-treatment impedance measurement over time;

comparing, with the processing circuitry, the average peak-to-peak amplitude of the baseline impedance measurement and the average peak-to-peak amplitude of the post-treatment impedance measurement;

generating, with the processing circuitry, an indication of efficacy based on the comparison, the indication of efficacy being:

sufficient lesion formation when the average peak-to-peak amplitude of the post-treatment impedance measurement is less than the average peak-to-peak amplitude of the baseline impedance measurement by at least a threshold amount; and insufficient lesion formation when the average peak-to-peak amplitude of the post-treatment impedance measurement is the same as the average peak-to-peak amplitude of the baseline impedance measurement, or the average peak-to-peak amplitude of the post-treatment impedance measurement is greater than the average peak-to-peak amplitude of the baseline impedance measurement by the threshold amount; and re-ablating the area of tissue with the treatment element if the indication of efficacy is insufficient lesion formation.

15. The method of claim 14, wherein the threshold amount is approximately 50%.

16. A medical system for assessing lesion formation, the medical system comprising:

a medical device having at least one impedance sensing electrode and a treatment element, the medical device being configured to ablate an area of tissue; and a control unit in communication with the medical device, the control unit including processing circuitry configured to:

recording a baseline impedance measurement from the area of tissue; record a post-treatment impedance measurement from the area of tissue after completion of ablating the area of tissue; identify at least one amplitude characteristic of the baseline impedance measurement and identify at least one amplitude characteristic of the post-treatment impedance measurement;

compare the at least one amplitude characteristic of the baseline impedance measurement and the at least one amplitude characteristic of the post-treatment impedance measurement; and generate an indication of efficacy based on the comparison, the indication of efficacy being one of sufficient lesion formation and insufficient lesion formation.

17. The medical system of claim 16, wherein the at least one amplitude characteristic is a peak-to-peak amplitude, the indication of efficacy being:

sufficient lesion formation when the peak-to-peak amplitude of the post-treatment impedance measurement is less than the peak-to-peak amplitude of the baseline impedance measurement by at least a threshold amount; and insufficient lesion formation when the peak-to-peak amplitude of the post-treatment impedance measurement is the same as the peak-to-peak amplitude of the baseline impedance measurement, or the peak-to-peak amplitude of the post-treatment impedance measurement is greater than the peak-to-peak amplitude of the baseline impedance measurement by the threshold amount.

18. The medical system of claim 17, wherein the threshold amount is approximately 50%.

19. The medical system of claim 17, wherein the at least one amplitude characteristic is an average peak-to-peak amplitude, the indication of efficacy being:

sufficient lesion formation when the average peak-to-peak amplitude of the post-treatment impedance measurement is less than the average peak-to-peak amplitude of the baseline impedance measurement by at least a threshold amount; and insufficient lesion formation when the average peak-to-peak amplitude of the post-treatment impedance measurement is the same as the average peak-to-peak amplitude of the baseline impedance measurement, or the average peak-to-peak amplitude of the post-treatment impedance measurement is greater than the average peak-to-peak amplitude of the baseline impedance measurement by the threshold amount.

20. The medical system of claim 19, wherein the threshold amount is approximately 50%.

* * * * *